United States Patent
Heuer et al.

(10) Patent No.: US 9,283,011 B2
(45) Date of Patent: Mar. 15, 2016

(54) BONE-ANCHORING OR BONE-CONNECTING DEVICE THAT INDUCES A STRAIN STIMULUS

(75) Inventors: Frank Heuer, Filderstadt (DE); Frank Trautwein, Filderstadt (DE); Jörg Franke, Magdeburg (DE); Michael Putzier, Stahnsdorf (DE); Ralph Kothe, Hamburg (DE); Guy Matgé, Mamer (LU); Ulf Liljenqvist, Müster (DE)

(73) Assignee: ACES INGENIEURGESELLSCHAFT MBH, Filderstadt (DE)

( * ) Notice: Subject to any disclaimer, the term of this patent is extended or adjusted under 35 U.S.C. 154(b) by 385 days.

(21) Appl. No.: 13/820,250

(22) PCT Filed: Sep. 1, 2011

(86) PCT No.: PCT/DE2011/050029
§ 371 (c)(1),
(2), (4) Date: May 13, 2013

(87) PCT Pub. No.: WO2012/045307
PCT Pub. Date: Apr. 12, 2012

(65) Prior Publication Data
US 2013/0231706 A1    Sep. 5, 2013

(30) Foreign Application Priority Data

Sep. 3, 2010 (DE) .......................... 10 2010 040 228

(51) Int. Cl.
*A61B 17/84* (2006.01)
*A61B 17/80* (2006.01)
(Continued)

(52) U.S. Cl.
CPC .................. *A61B 17/84* (2013.01); *A61B 17/80* (2013.01); *A61B 17/8625* (2013.01);
(Continued)

(58) Field of Classification Search
CPC ..... A61B 17/80; A61B 17/864; A61B 17/8685
USPC .................................. 606/280–299, 300–331; 623/17.11–17.16
See application file for complete search history.

(56) References Cited

U.S. PATENT DOCUMENTS 6,395,035 B2 * 5/2002 Bresina et al. ............. 623/17.15
2005/0228503 A1   10/2005 Gundolf
(Continued)

FOREIGN PATENT DOCUMENTS

DE    908906    4/1954
DE    19816828  10/1999
(Continued)

OTHER PUBLICATIONS

Sarkar, et al., "Bone Formation in a Long Bone Defect Model Using a Platelet-Rich Plasma-Loaded Collagen Scaffold," Biomaterials, vol. 27, pp. 1817-1823 (2006).
(Continued)

*Primary Examiner* — Christopher Beccia
(74) *Attorney, Agent, or Firm* — Hoffmann & Baron, LLP

(57) ABSTRACT

The invention relates to an implant in the form of a bone-connecting device with an implant carrier, having at least two structure carriers for stimulating bone growth, the structure carriers can move relative to one another so that, due to a loading of the implant, a relative movement of the structure carriers occurs, the structure carriers furthermore contain structure elements that are arranged so that they define a plurality of partially open intermediate spaces, wherein a volume defined by these intermediate spaces and an immediate environment is deformed by the implant load, and a strain in the intermediate spaces and its immediate environment resulting from the deformation lies in the physiological range for bone growth.

12 Claims, 7 Drawing Sheets

(51) Int. Cl.
*A61B 17/86* (2006.01)
*A61F 2/44* (2006.01)
*A61F 2/28* (2006.01)
*A61F 2/30* (2006.01)

(52) U.S. Cl.
CPC .............. *A61B 17/8685* (2013.01); *A61F 2/44* (2013.01); *A61B 17/864* (2013.01); *A61F 2/4455* (2013.01); *A61F 2002/286* (2013.01); *A61F 2002/2835* (2013.01); *A61F 2002/30563* (2013.01); *A61F 2002/30565* (2013.01); *A61F 2310/00796* (2013.01); *A61F 2310/00976* (2013.01)

(56) References Cited

U.S. PATENT DOCUMENTS

2007/0270970 A1* 11/2007 Trieu ........................ 623/17.14
2009/0118836 A1* 5/2009 Cordaro ..................... 623/17.16

FOREIGN PATENT DOCUMENTS

| DE | 20015265 | 1/2001 |
|---|---|---|
| DE | 10215996 | 11/2003 |
| DE | 10348329 | 2/2005 |
| EP | 0950389 | 10/1999 |
| EP | 1430846 | 8/2006 |
| EP | 1943986 | 7/2008 |
| WO | WO9324092 | 12/1993 |
| WO | WO0032125 | 6/2000 |
| WO | WO2004017857 | 3/2004 |

OTHER PUBLICATIONS

Baas, et al., "In Vitro Bone Growth Responds to Local Mechanical Strain in Three-Dimensional Polymer Scaffolds," Journal of Biomechanics, vol. 43, pp. 733-739 (2010).

Frost, "From Wolff's Law to the Utah Paradigm: Insights About Bone Physiology and Its Clinical Applications," The Anatomical Record, vol. 262, pp. 398-419 (2001).

Ignatius, et al., "Tissue Engineering of Bone: Effects of Mechanical Strain on Osteoblastic Cells in Type I Collagen Materials," Biomaterials, vol. 26, pp. 311-318 (2005).

Lu, et al., "Do Bending, Twisting, and Diurnal Fluid Changes in the Disc Affect the Propensity to Prolapse? A Viscoelastic Finite Element Model," Spine 21, vol. 22, pp. 2570-2579 (1996).

Reigstad, et al., "Improved Bone in Growth and Fixation with a Thin Calcium Phosphate Coating Intended for Complete Resorption," Journal of Biomedical Materials Research, Part B, pp. 1-25 (2007).

* cited by examiner

BONE-ANCHORING OR BONE-CONNECTING DEVICE THAT INDUCES A STRAIN STIMULUS

TECHNICAL FIELD

The invention relates to an implant in the form of a bone-anchoring or bone-connecting device that can preferably be implanted to stabilise the spinal column. The implant can have a high intrinsic stiffness, which permits a dimensioning and design to provide high fatigue strength and implant durability. Due to the formation and arrangement according to the invention of surface structures on a structure carrier there can be generated—despite the high implant stiffness—a physiologically effective strain stimulus along the implant surface and between individual elements within the implant. The surface elements are dimensioned in such a way and are adapted to the load as well as stiffness of the implant so that a physiological strain stimulus, that is a strain stimulus that stimulates bone growth, is generated.

PRIOR ART

For surgical treatment, in particular in an osteosynthesis or stabilisation of spondylopathies, a large number of implants with screwable anchoring devices are known (e.g. "pedicle screws"). The problem of the screws becoming loose is often described, which is a consequence of the so called "stress shielding". The effect of the stress shielding is attributed to the biological-biomechanical principles of the mechanical stimulation of bone growth (Ignatius, 2005; Baas, 2010). A functional connection (1) was described by Frost in a review (Frost 1987) (FIG. 1). If for example a strain of less than 800 µstrain (corresponding to 0.08%) is applied to the bone tissue, so called "remodelling" (10) of the bone occurs. In remodelling bone is prepared and reconstructed, though the bone mass and bone strength tend to decrease. Starting at a strain of 800 to 1,500 µstrain an equilibrium state exists between the remodelling and the modelling (11). Here bone is equally broken down and rebuilt, the bone mass and bone strength remaining unchanged. Starting at a strain of 1,500 µstrain predominantly bone construction ("modelling") takes place, which reaches its maximum at ca. 2,000 µstrain (12). If the strain is increased further, the bone becomes necrotic and can lose its structural integrity. A bone breaks above ca. 15,000 µstrain (13). Thus, the typical bone, for example the tibia, has a safety factor of about 5 to 7 between the maximal typical deformation (maximum 2,000 to 3,000 µstrain) and its fracture limit (ca. 15,000 µstrain). If a screw is now placed in the bone, structural differences exist. A screw produced from a titanium alloy has an E modulus of ca. 105 GPa. Bone has an E modulus of ca. 22 GPa at the corticalis and <1 GPa at the spongiosa (Lu, 1996). On account of these differences the many times stiffer screw stabilises the surrounding bone tissue, so that it screens a natural strain stimulus from the bone tissue and promotes the negative remodelling process in the vicinity of the screw. A decreasing bone substance and/or strength thus provokes screw loosening, which often require an additional revision operation.

A general method of stimulating bone growth with a strain stimulus was shown in WO9324092A1, 1992. Here the method is based however on a systematic, external loading that acts simultaneously on all bones and utilises the force of gravity and inertia.

From EP1430846B1, 2002 it is known that bone growth can be promoted with an increase in the screw surface and a thereby created porosity. A disadvantage of this structure is the significantly reduced cross-section, the generation of stress peaks in the region of the screw holes, and thus the reduced fatigue strength of the bone anchor.

From WO2004017857A1, 2002 a method is known with which anchoring devices are placed in the bone and are then subjected to ultrasound in order to liquefy a plastic material by increase in temperature, which then flows into the bone interstices and thereby effects a mechanical connection. The material described there is relatively soft however, and is therefore rather unsuitable for an osteosynthesis or load-bearing implants. Furthermore, there is the danger of localised damage to the tissue or bone due to the temperature effect.

In WO0032125A1, 1998 a thread shape was proposed, with which the bone is compressed when the screw is screwed in. This increases the primary stability, but this arrangement is subject in the same way to the stress shielding described in the introduction.

From DE908906, 1954 a spring-loaded bone screw is known, which is intended to press the bone fragments together with a permanent pretensioning. Although the stress shielding is largely thereby avoided, nevertheless it is doubtful whether such a screw has the necessary durability for stabilising bones.

Furthermore there exist some variants of screw systems in which bone cement is injected in order to augment the screw in the weakened bone (for example in osteoporosis). The cement injection is irreversible and has numerous potential risks (undesirable leakage of cement into the vertebral channel, intervertebral disc or the vascular system, necrotisation due to high local reaction temperatures, corrosion between the implant and X-ray contrast medium).

From Reigstad, 2007, it is known that the coating of screws increases bone growth after a short healing time of 12 weeks. The additional coating with (tri)calcium phosphate and hydroxyl apatite shows some success. The only a few µm thick layer is however completely resorbed after the healing phase (Reigstad, 2007). At this point in time there are no long-term observations that could rule out a bone breakdown (remodelling) after the layer resorption. A bone reduction at the coated screw would be expected after the coating has been resorbed. Apart from the questionable long-term use, the coating involves significant additional costs in the production of such bone anchors. In addition the costs associated with the approval process of an implant that is "active" due to the coating are significantly higher compared to an uncoated implant.

In the past a plurality of spring-elastic and dynamic implants had been proposed, which on account of a reduced intrinsic stiffness allow higher strains (micro-movements) on the bone (DE10348329B3, 2003; EP1943986A2, 2005). This strain is said to stimulate bone growth. These approaches have the disadvantages however of a reduced fatigue strength and a high variability of the strain depending on the load, which can easily lead to a strain far beyond the ideal strain stimulus for the bone structure.

A further clinical phenomenon is the failure of bone to heal in a bone defect that has exceeded a specific size ("critical size defect"). Here the strain stimulus between the bone fragments is absent. From clinical practice it is known that various bone replacement materials are used in order to bridge the bone gap. However, most bone replacement materials are limited in that they cannot withstand the loads and degrade mechanically unsatisfactorily, and raise the local acid level (Sarkar, 2006), which is a disadvantage in particular in implants with reduced intrinsic stiffness.

A stiff implant for reducing the bone defect size with at the same time a controlled mechanical strain stimulation over the fusion stretch is not known.

DESCRIPTION OF THE INVENTION

Technical Object

The object of the present invention is to provide an implant that can be connected to the bone in order to transmit loads and through a relative movement of suitable structures connected to the implant exerts a physiological strain stimulus on the tissue, with the aim of improving and/or accelerating the bone healing.

Technical Solution

This object is achieved in that lamella-like surface elements or structures (hereinafter also termed structure carriers) are arranged on the surface of an implant carrier. The structure carriers are largely decoupled from the implant carrier, but are connected at least at one point to the implant carrier, in particular in the region of the interfaces for the joining to the existing bone. In a preferred embodiment a plurality of structure carriers are in each case joined alternately to opposite sides of the interfaces of the implant carrier. The structure carriers can also contain depressions or openings (pores), in which the bone cells can anchor. If the implant is subjected to load by the patient, the structure carriers execute relative movements. The stiffness of the implant carrier and the division and intermediate space of the structure carriers as well as their maximum possible displacement are designed so that the strain stimulus exerted by the structure carriers on the tissues leads to the (accelerated) formation of bone cells. The arrangement according to the invention of the structure carriers and structures on the structure carrier can equally be used in bone-anchoring devices and bone-bridging elements, and in each case achieves the object of stimulating bone growth in the region of the implant.

Advantageous Effects

An advantageous feature of the present invention is that the implant according to the invention exerts a strain stimulus on the surrounding bone tissue and induces the "modelling" process. This increases the anchoring strength with the bone and therefore reduces implant loosening. A major advantage is that the relatively high, physiologically effective strains on the surface can be generated with an implant that has at the same time a high intrinsic stiffness. The problem of the deficient bone bridging in large defect sites on account of the lack of a strain stimulus is solved by the invention. Furthermore, the arrangement of the structure carriers has hardly any effect on the fatigue strength of the implant, since they are decoupled from the load-bearing implant carriers. The arrangement of the structure carriers and their structures enables various strain regions to form. For example, linear strain regions can be combined with non-linear regions or with regions of higher strains. Due to the mechanical bone growth stimulation the present invention provides an alternative to implant coatings and the use of expensive biological preparations for stimulating bone growth. Apart from the better implant and anchoring stability and higher fusion rates combined with improved bone quality, cost advantages can be achieved with the implant according to the invention.

WAYS OF IMPLEMENTING THE INVENTION

The technical solutions are described hereinafter by way of example. These should be interpreted as means for illustrating the underlying concept and should not be regarded as limited to the respective specific representation.

Figure 1:
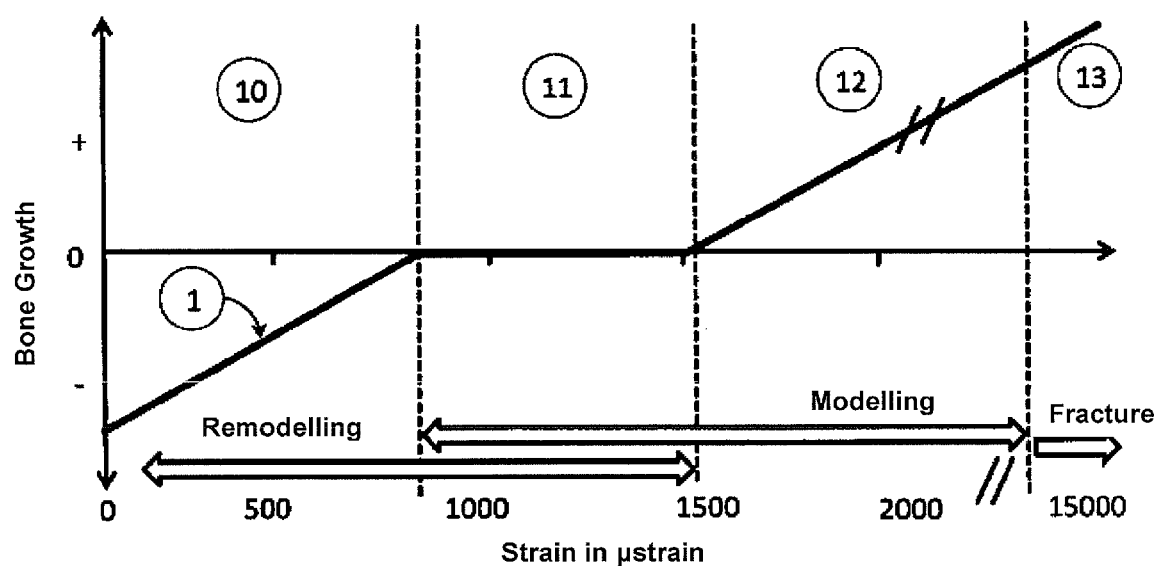
FIG. 1 shows the functional connection between bone growth and the applied strain in the bone tissue.
Figure 2:
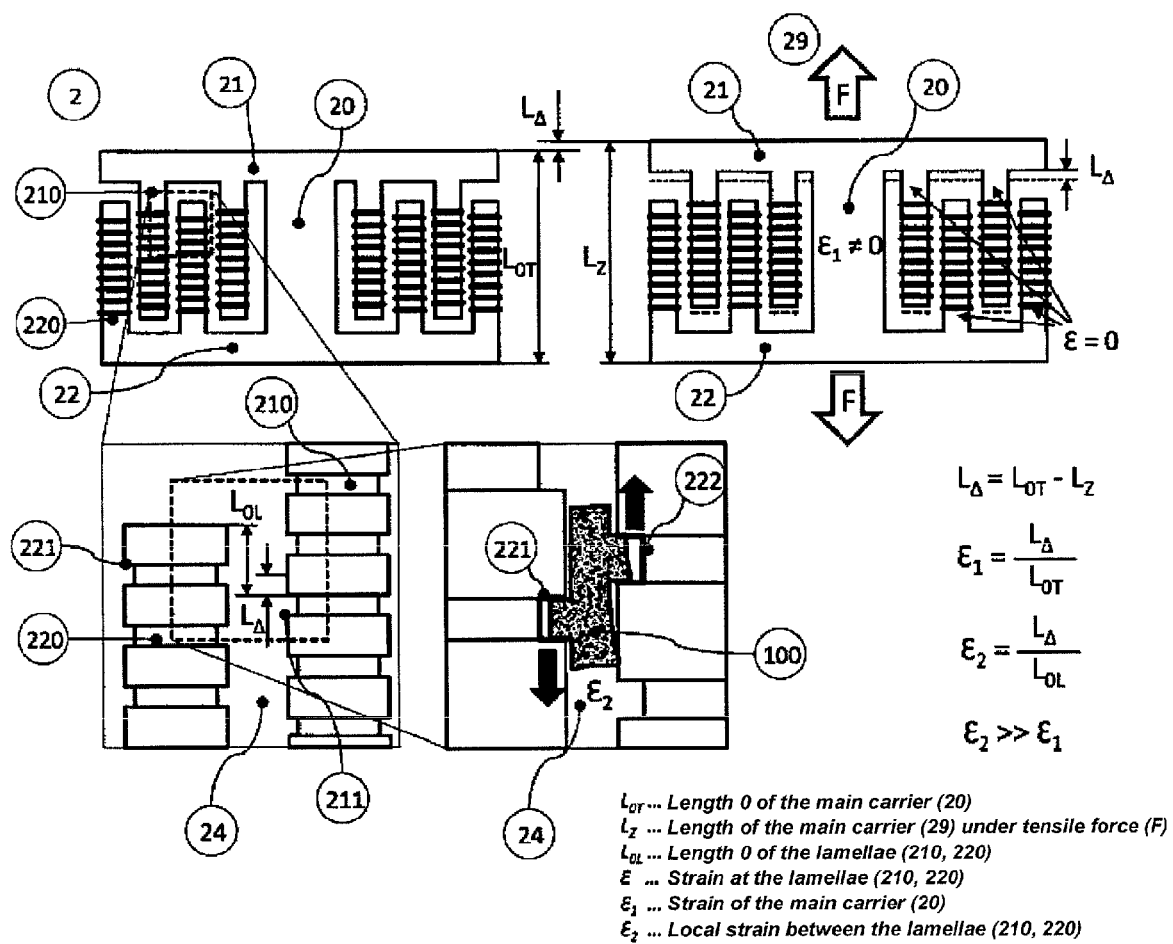
FIG. 2 illustrates the generation of the local strain at the implant surface.

The implant (2) according to the invention consists of at least one implant carrier (20) with in each case at least one pair of implant interfaces (21, 22) via which the mechanical load (F) is introduced into the implant, as well as at least one structure carrier (210) having a structure in the form of regular or irregular lamellae, lattices, shaped parts, recesses, bores or cavities (211, 221). The loading of the implant can in this connection occur as a result of the daily activities of the patient, specific loads in the form of exercises (physiotherapy), or through an external or internal mechanical loading. If two or more structure carriers are used, one structure carrier is termed the first structure carrier (210) and the second the second structure carrier (220) (FIG. 2). The interfaces (21, 22) have respective structure carriers (210, 220) facing towards them and thus connected to them. The structure carriers (210, 220) are furthermore characterised in that they have a topological structure (211, 221) on or in the surface. These structures (211, 221) can be generated for example by pores, bores, grooves, slits, openings, textures, webs, shaped portions, roughened portions, coatings or other elements that form a structure for generating height differences. They have the task of subjecting the bone material that is located in the overlapping region between the structure carriers or is formed there (24), to a local strain and thereby stimulating bone growth and thus osseointegration.

If two or more interfaces (21, 22) are connected to the implant carrier (20), then the structure carriers (210) can be arranged so that, when the implant is loaded, they move towards one another, away from one another, or move past one another. A gap or a device for ensuring a minimum distance between the structure carriers and their surfaces can prevent unphysiologically high strains or squeezing of the tissue and in this way prevent the destruction of the forming tissue.

If a force or a torque (29) acts via the interfaces (21, 22) on the whole implant (20), the implant carrier (20) deforms, which is characterised by the strain $\epsilon_1$. The structure elements that are fastened to the first (210) and second (220) structure carriers experience themselves no noticeable internal deformation ($\epsilon=0$). The structures of the structure carriers, hereinafter termed lamellae for simplicity, are displaced relative to one another by the total contribution of the implant deformation ($L_A$). If this total displacement $L_A$ is related to the distance $L_{OL}$ between the depressions of two opposite lamellae, the result is a localised strain $\epsilon_2$ in the intermediate space (24), which lies for example in the ratio $L_A/L_{OL}$ orders of magnitude above the actual implant strain $\epsilon_1$. The intermediate space (24) is colonised with tissue or filled with bone material and thus forms the starting point for bone growth. By a suitable choice of the structure size $L_{OL}$ the local strain resulting from the relative displacement of the lamellae (210, 220) can, in combination with the stiffness of the implant carrier (20), be adjusted practically arbitrarily. Preferably the maximum strain of the tissue in the intermediate space in combination with the structure size $L_{OL}$ is chosen, for example according to Frost 1987, so that the local strain stimulus on the bone cells lies in the range for maximum bone structure. The change in shape or deformation of the implant carrier (20) occurs largely in the elastic, fatigue-free load-bearable region. Although the implant carrier need not differ, or only slightly, in terms of its mechanical properties and elasticity from conventional rigid implants, the configurations according to the invention are able to generate and transfer to the surrounding tissue, strains that are physiologically effective for the bone structure.

Figure 3:
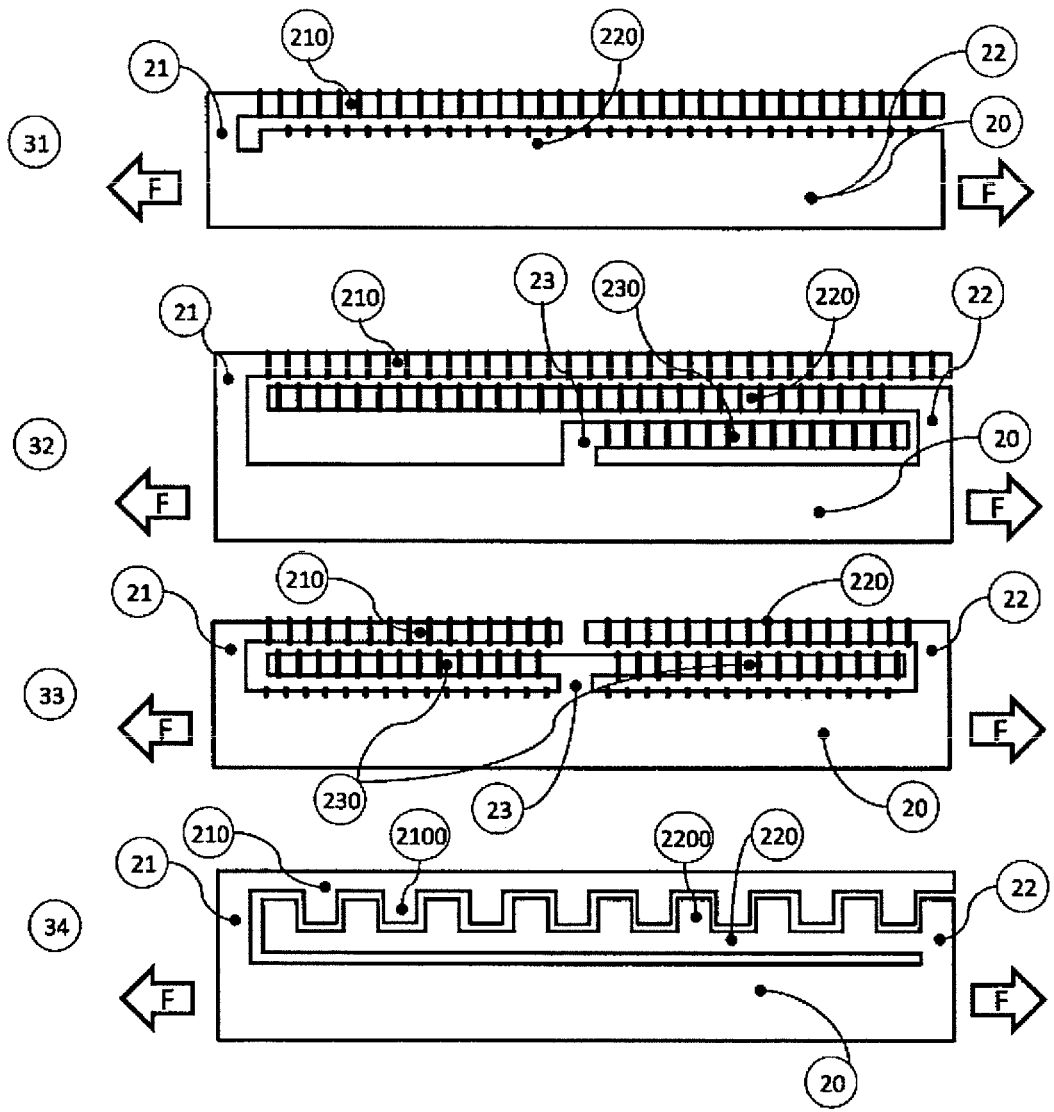
FIG. 3 shows various arrangements of the surface lamellae.

In a further modification of the invention the arrangement of the lamellae can be varied in order to combine different strain behaviours with one another (FIG. 3). As a first example (31) it is shown that the use of only one structure carrier is already able to generate a plurality of locally different strains along the implant surface, wherein on account of the co-use of the implant carrier a non-linear behaviour of the local strain takes place. In the illustrated example the local strain increases in proportion to the distance of the connection between the implant carrier and structure carrier.

In the second example (32) a third implant interface is shown, which is termed middle interface (23). With the arrangement of the interfaces (21, 22, 23) and the structure carriers (210, 220, 230) specific strain regions can be adjusted. On the one hand a non-linear behaviour, as shown in (31), is produced between the implant carrier (20) and the structure carrier (230). In addition a uniform strain is generated between the structure carriers (220) and (230), which can be doubled once more in the intermediate space between (210) and (220). Thus, for example, three structure carriers can be arranged so that their strain regions can be added (32). In the example (33) strain regions can be reduced by joining the connecting site of the structure carrier (23) for example centrally to the implant carrier (20). In a further example (34) it is shown that the structure carriers (210, 220) can have further structural embodiments, with the aim of transmitting the overall deformation ($L_A$) over a large surface to the bone tissue. The combination of elements of different structure size, for example a lamella-like structure with a roughening on the surface, appears to be particularly suitable for this purpose.

In order to accelerate and further improve the bone formation and the healing of the implant according to the invention, the structure elements (20, 21, 22), the lamellae (210, 220, 230) and in particular the intermediate spaces (24) can additionally contain an osteoinductive and/or or osteoconductive material or can be coated therewith. Examples of such materials are hydroxyl apatite, (tri)calcium phosphate or proteins, such as for example BMP or RGD.

Figure 4:
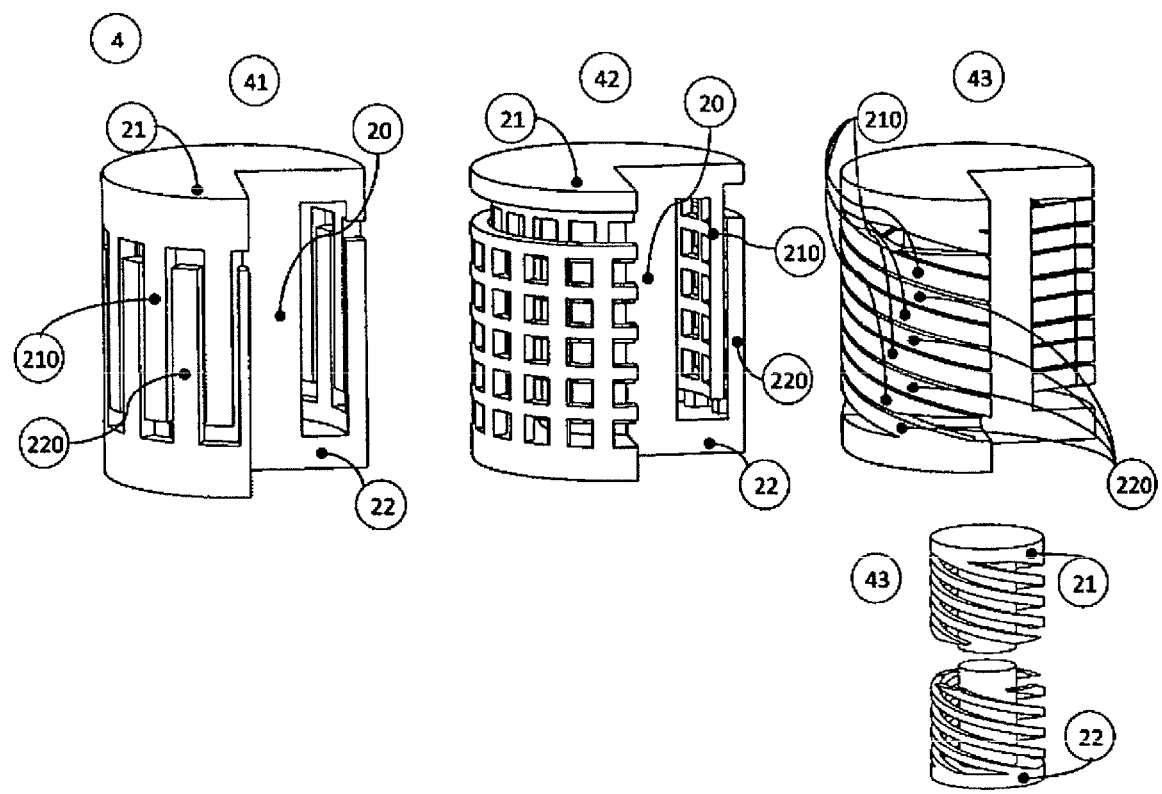
FIG. 4 shows an example of a bone-bridging element.

An example of a bridging element for closing large bone gaps or for fusing vertebral bodies is illustrated in FIG. 4. Here it is shown by the example of a vertebral body replacement implant that the structure carriers (210, 220) transmit the deformation of the implant carrier (20) to the implant surface. In this connection the structure carriers (210, 220) can be arranged longitudinally interengaging one another (41) or radially overlapping one another (42), so that the structure carriers only consist of radial components (only transverse to the load direction). Both configurations (41, 42) can also be combined with one another.

A further configuration is illustrated in (43), in which the structure carriers (210, 220)—seen from their surface—move inclined to one another, so that the relative movement of the structure carrier has a shear component as well as an axial displacement component. Here too the two structure carriers (210, 220) are respectively joined to only one implant interface (21, 22), so that there is no substantial deformation of the structure carriers themselves, but instead a relative displacement of the tissue between the structure carriers. If one disregards a possible slight deformation of the structure carriers, then the relative displacement of the tissue corresponds in this case to the displacement of the interfaces (21, 22). Furthermore the surface structures (210, 220) can also be arranged crosswise (for example by an interengaging spatial lattice structure), corresponding to a mixed shape of (42) with (43).

Figure 5:
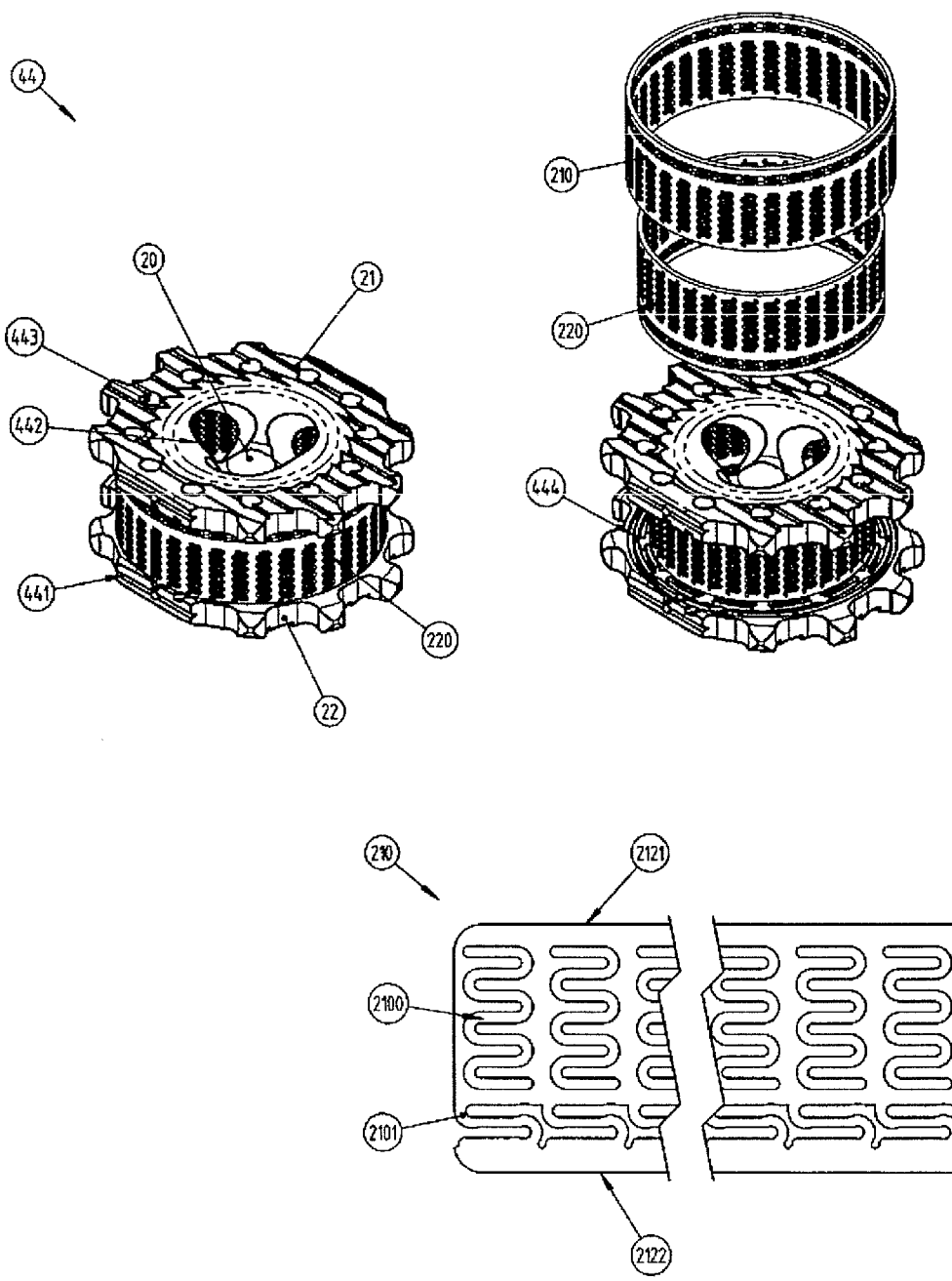
FIG. 5 shows the use of individual surface lamellae on an implant.

FIG. 5 shows an intervertebral implant (44), which consists of an implant carrier (20) and a plurality of layers of structure carriers (210, 220). The implant carrier (20) is configured so that it has one or more openings (442), which serve for filling with bone (replacement) material and/or for nutrient exchange (443). In addition the implant can have a fastening capability (441) for connection to an implant instrument. The implant furthermore has an upper (21) and a lower (22) interface to which the structure carriers (220) are joined. A bar guide (444) is shown here by way of example as a possible form of connection to the structure carriers. In this embodiment the structure carriers can be made of a metal sheet. The structure carriers (210, 220) are inserted into the implant (44) for the installation along the bar guide (444). So that the structure carriers (210, 220) together with their two edges (2121, 2122) are held in the bard guide (444) of the implant carrier (20) and thereby prevented from falling out, a set of springs (2101) can be provided in the plates. The springs perform the task of pressing the metal sheet (210), formed as structure carrier, firmly against one of the interfaces, so that a movement of the interface occurs with a movement of the structure carrier. Obviously the structure carriers can also be connected by an alternative positive engagement, frictional or adhesive connection to the interfaces (21, 22). The structure carriers, which are as a rule arranged in pairs, are in this connection firmly connected, ideally alternately, to respectively one of the interfaces (21, 22).

Figure 6:
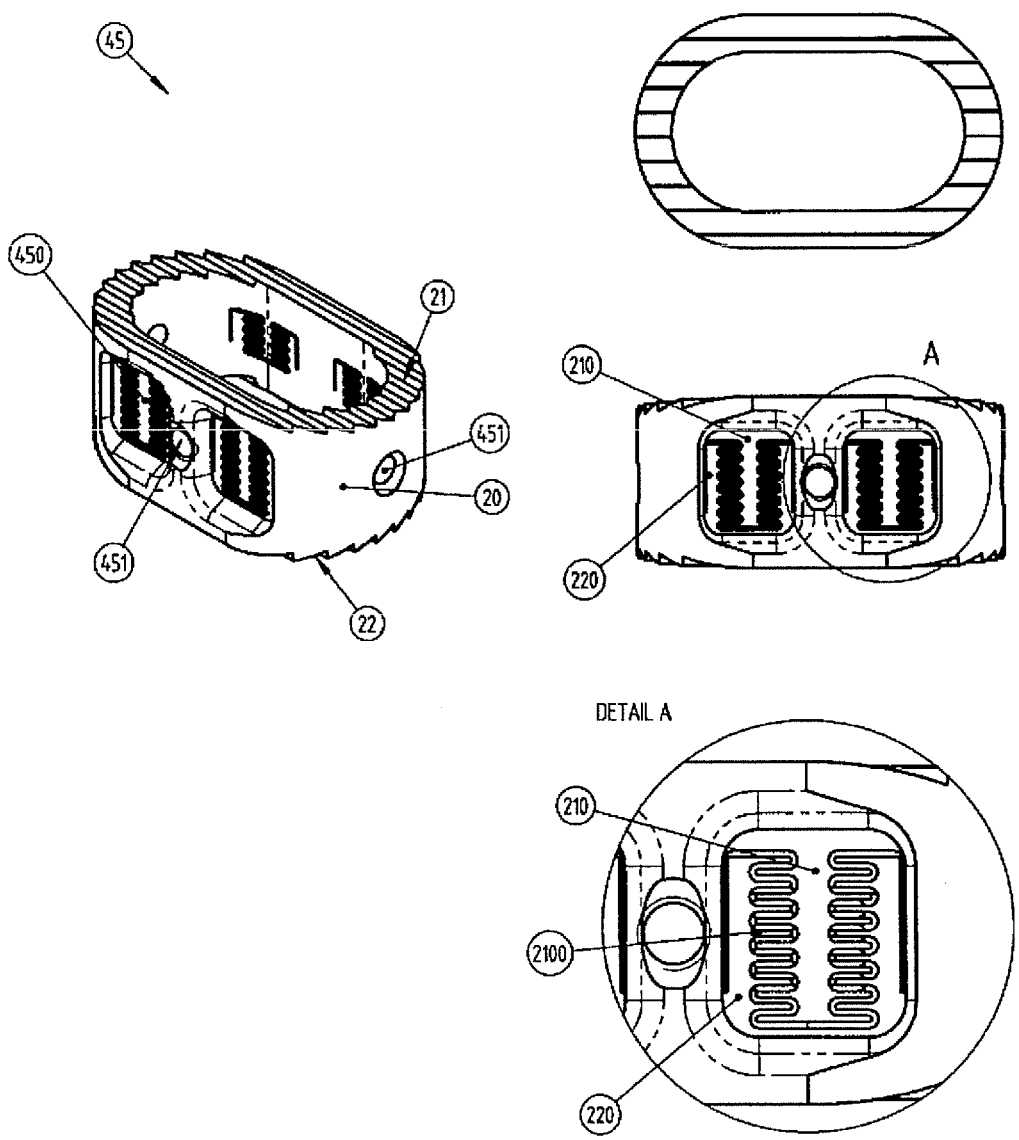
FIG. 6 shows an intervertebral disc implant with the bone growth-stimulating lamellae.

A further intervertebral implant (45) with a shape dependent on the anatomy of the spinal column, with an upper (21) and a lower (22) interface, is shown in FIG. 6. The intervertebral implant consists of the implant carrier (20), which can include a receptacle (451) for an implant instrument. Recesses (450) are formed in the implant carriers (20), which are filled with one or a plurality of structure carriers (210, 220). The structure carriers identified by the reference numeral (210) are joined to the upper interface (21), and the structure carriers with the reference numeral (220) are joined to the lower interface (22). The structure carriers formed in one piece in this example are separated by meander-shaped cut-out sections (2100) into two function regions (210, 220). The cut-out gap as well as the meander shape serves in this case to generate the intermediate space for transferring the strain to the tissue.

A further advantageous configuration is obtained by the integral connection of a structure carrier to the implant carrier and combination with at least one second structure carrier that can move relative to the implant carrier. In this case the division between the load-bearing elements and elements that exert a local strain stimulus on the tissue is achieved by a corresponding shape of cut-out sections, openings or connecting elements.

Figure 7:
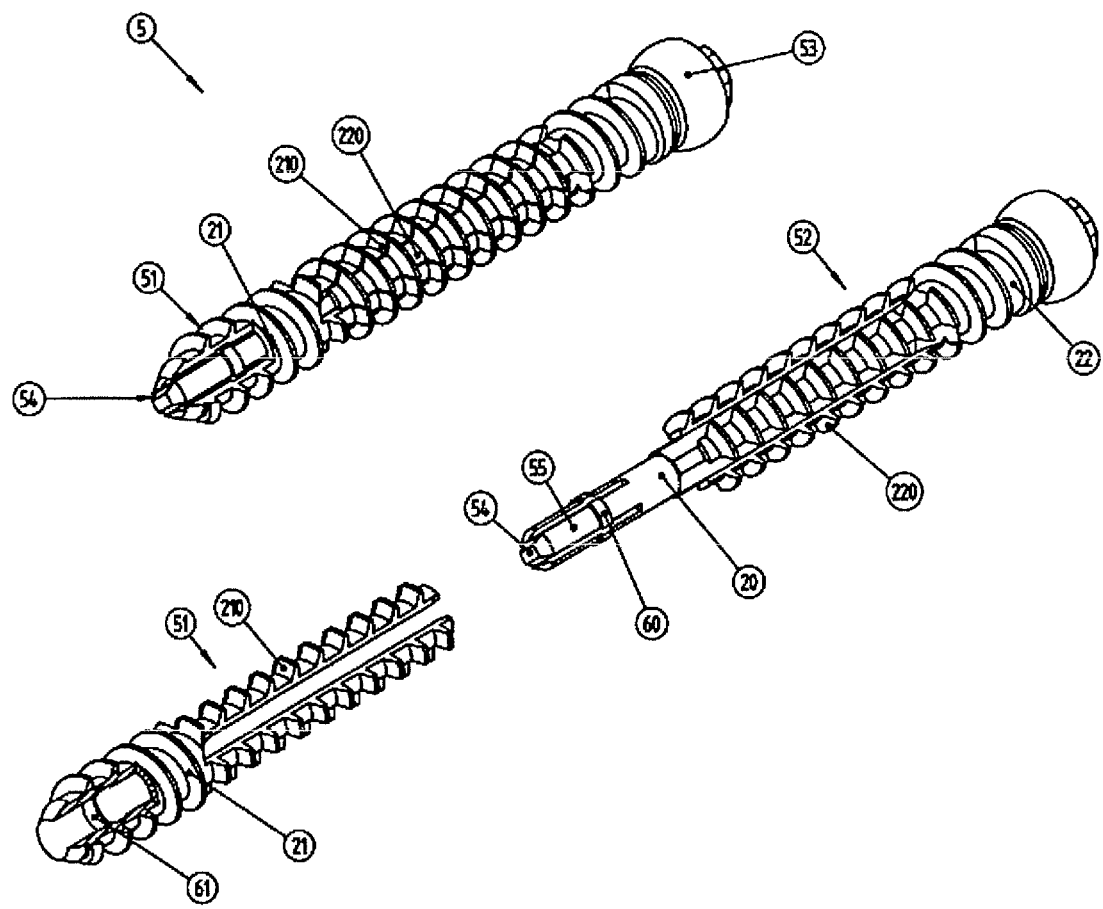
FIG. 7 illustrates an example of a bone-anchoring device.

An exemplary implementation of this approach is shown in FIG. 7 with the aid of a bone-anchoring device, as is used in particular as a pedicle screw in spinal column implants. The pedicle screw (5) consists of a distal shaft part (51), a proximal shaft part (52), a screw head (53), an optional through opening (54) and a connecting plug (55). The implant carrier (20) is connected at the connection site (55) to the structure carrier (21). The connection site (55) can be configured so that it allows a rigid, spring-elastic or, as in the illustrated example, a path-limited relative movement between the implant carrier and structure carrier. To this end a groove (61) is located for example in the bore (54) of the structure carrier (21), the groove being somewhat wider than the shoulder (60) of the implant carrier (20) engaging therein. In the illustrated example the implant carrier (20) also has a screw head (53) for connection to further components. The distal shaft part (51) corresponds to the first interface (21), which in turn performs through the thread flanks the function of the first structure carrier (210). The second interface (22) with its associated structure carrier (220) and the thread flanks located thereon is disposed on the proximal shaft (52). If the screw (5) is subjected to a tensile or bending load, only a relative movement in the longitudinal direction between the flanks of the structure carriers (210, 220) can occur, limited by the play between the groove (61) and shoulder (60). Due to the overlapping, inter-sliding arrangement of the two structure carriers their relative movement can now be transmitted to the bone located between the thread flanks and can exert a strain stimulus on the bone.

The invention claimed is:

1. An implant in the form of a bone-connecting device comprising:
    an implant carrier body having a first end and an opposite second end, each end for applying a force and joining to an existing bone structure;
    a structure carrier connected to the first end of the carrier body and having a length extending in a direction toward the second end of the carrier body, wherein an intermediate space is defined between the structure carrier and the carrier body, wherein the structure carrier is formed with a structured surface comprising structure elements disposed within the intermediate space defined between the structure carrier and the carrier body, and wherein the surface structure of the structure carrier in the intermediate space is configured so that the intermediate space can be colonized by tissue, and wherein the surface structure of the structure carrier moves relative to the carrier body as a result of a mechanical loading of the first and second ends of the carrier body.

2. An implant according to claim 1, wherein the structured surface is structured with a structure size in the range from 0.2 to 100 μm.

3. An implant according to claim 1, wherein the structure carrier or a connection area of the structure carrier having a side facing the interfaces comprise a region of lower stiffness, and on an opposite side a region of higher stiffness.

4. An implant according to claim 1, wherein the structure carriers contain a substance for accelerating bone formation, and/or are coated, and/or enriched with a substance for accelerating bone formation and/or the intermediate space is filled with a substance for accelerating bone formation.

5. An implant according to claim 1, wherein the strain in the intermediate space resulting from a loading of the implant is in a range between 100 and 15,000 μm/m.

6. An implant according to claim 1, wherein a maximum relative movement of the structure carriers is limited by one or a plurality of stop means.

7. An implant according to claim 1, wherein a maximum relative movement of the structure carriers is limited to values between 0.1 μm and 200 μm.

8. An implant according to claim 1, wherein the strain in the intermediate space resulting from a loading of the implant during a healing phase is in a range between 500 and 10,000 μm/m.

9. An implant according to claim 1, wherein a spacing of the structure elements on the structure carriers, and a spacing between the structure elements and a stiffness of the implant carrier are adapted to an expected mechanical loading of the implant to achieve a strain on the tissue located in the intermediate space, wherein the strain is within a range favorable for bone growth.

10. An implant according to claim 1, wherein the structure elements are self-supporting and thereby simultaneously perform the function of the structure carriers.

11. An implant according to claim 1, wherein the structure carriers include a structured surface selected from the group lamellae, lattices, protrusions, teeth, recesses, bores, pores, textures, roughened sections, coatings or cavities.

12. An implant according to claim 11, wherein the structured surface includes a plurality of regular structures having a structure size in the range from 0.2 to 10 mm.

* * * * *